United States Patent
Fayad et al.

(10) Patent No.: US 7,764,814 B2
(45) Date of Patent: Jul. 27, 2010

(54) DISPLAY AND ANALYSIS OF MULTICONTRAST-WEIGHTED MAGNETIC RESONANCE IMAGES

(75) Inventors: Zahi A. Fayad, Larchmont, NY (US); Daniel D. Samber, New York, NY (US); Venkatesh Mani, Parsippany, NJ (US); John T. Fallon, Rowayton, CT (US); Vitalii Itskovich, Brooklyn, NY (US); Chara Itskovich, legal representative, Brooklyn, NY (US)

(73) Assignee: Mount Sinai School of Medicine, New York, NY (US)

( * ) Notice: Subject to any disclaimer, the term of this patent is extended or adjusted under 35 U.S.C. 154(b) by 944 days.

(21) Appl. No.: 10/562,745

(22) PCT Filed: Jun. 30, 2004

(86) PCT No.: PCT/US2004/021116

§ 371 (c)(1),
(2), (4) Date: Oct. 26, 2006

(87) PCT Pub. No.: WO2005/008257

PCT Pub. Date: Jan. 27, 2005

(65) Prior Publication Data

US 2007/0053554 A1    Mar. 8, 2007

Related U.S. Application Data

(60) Provisional application No. 60/486,044, filed on Jul. 10, 2003.

(51) Int. Cl.
*G06K 9/00* (2006.01)
(52) U.S. Cl. .................................. 382/128; 382/131
(58) Field of Classification Search ................. 382/128, 382/130, 131, 133, 162, 181; 600/413, 420
See application file for complete search history.

(56) References Cited

U.S. PATENT DOCUMENTS 4,945,478 A    7/1990  Merickel et al.
6,580,936 B2   6/2003  Muraki et al.

OTHER PUBLICATIONS

International Search Report and Written Opinion Under Date of Mailing of Jan. 31, 2005, in connection with International Patent Application No. PCT/US2004/021116.

*Primary Examiner*—Duy M Dang
(74) *Attorney, Agent, or Firm*—Quarles & Brady LLP

(57) ABSTRACT

A multicontrast-weighted acquisition of three images is performed with an MRI system. Each image is normalized and then mapped to a separate color channel. A composite color image is formed by combining all the color channels, and this image is displayed or analyzed to identify different tissue types therein.

19 Claims, 9 Drawing Sheets

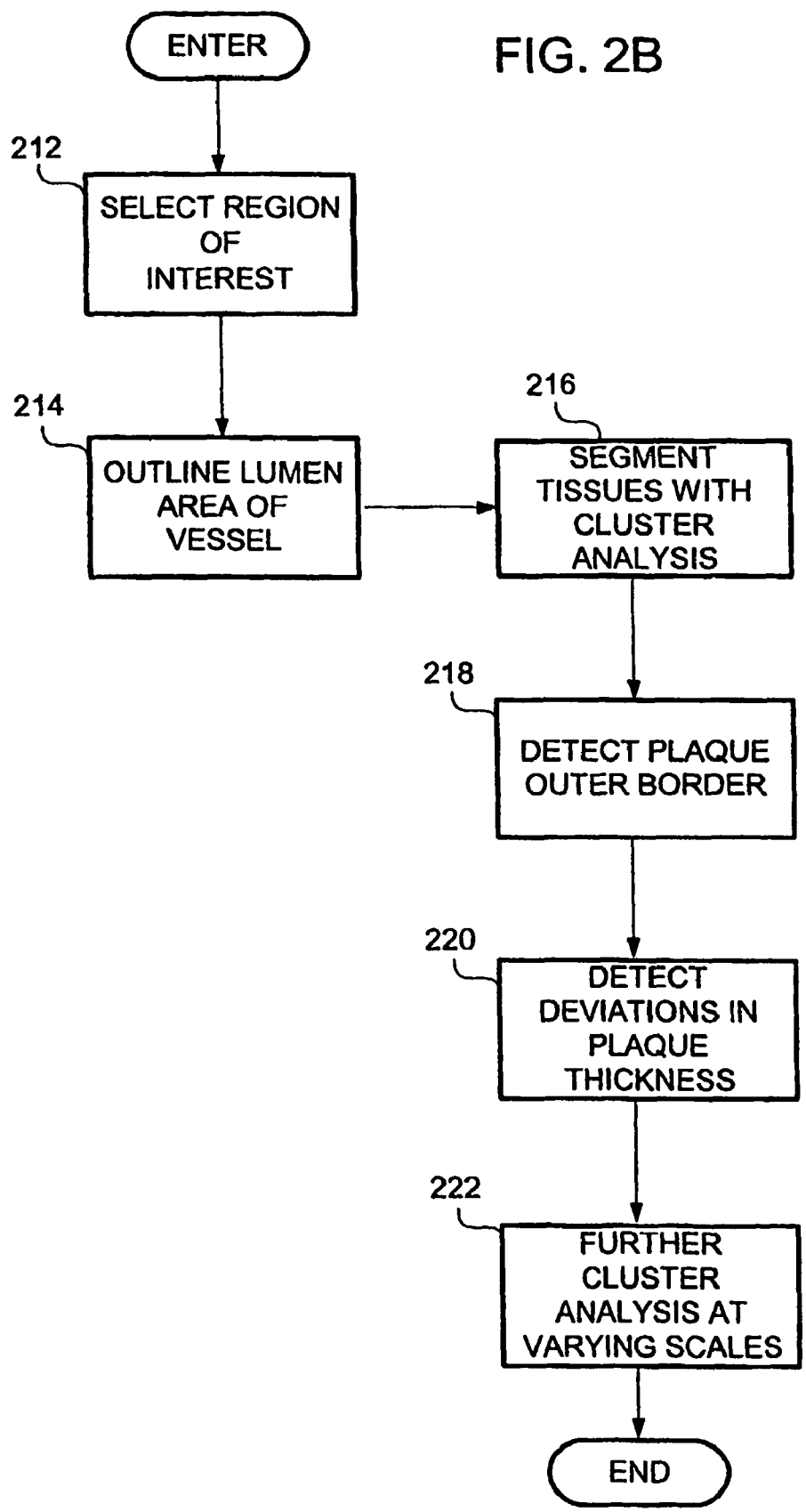

FIG. 8

| Tissue Type \\ Comparison Type | Loose Fibrous, N=11 | | | Media, N=22 | | | Fibro-cellular, N=20 | | | Lipid/necrotic core, N=7 | | | Thrombus, N=3 | | | Dense fibrous, N=11 | | |
|---|---|---|---|---|---|---|---|---|---|---|---|---|---|---|---|---|---|---|
| | r | bias | lim | r | bias | lim | r | bias | lim | r | bias | lim | r | bias | lim | r | bias | lim |
| Histopathology Tracing & Cluster-analyzed MRI | .78 | 2% | ±8% | .84 | 0% | ±8% | .89 | 0% | ±6% | .76 | 2% | ±6% | .98 | 3% | ±3% | .83 | 1% | ±5% |
| Histopathology Tracing & Cluster-analyzed MRI – reduced resolution | .69 | 3% | ±9% | .61 | 2% | ±11% | .55 | 5% | ±13% | .77 | 0% | ±6% | .85 | 4% | ±4% | .74 | 3% | ±9% |
| Histopathology Tracing & Color-space Matching | .58 | 4% | ±9% | .51 | 4% | ±14% | .40 | 2% | ±9% | .37 | 6% | ±11% | .60 | 4% | ±7% | .23 | 2% | ±11% |

DISPLAY AND ANALYSIS OF MULTICONTRAST-WEIGHTED MAGNETIC RESONANCE IMAGES

CROSS-REFERENCE TO RELATED APPLICATIONS

This application claims the benefit of U.S. Provisional patent application Ser. No. 60/486,044 filed on Jul. 10, 2003 and entitled DISPLAY AND ANALYSIS OF MULTICONTRAST-WEIGHTED MAGNETIC RESONANCE IMAGES".

STATEMENT REGARDING FEDERALLY SPONSORED RESEARCH

This invention was made with government support under Grant No. 1RO1HL071021 awarded by the National Institute of Health. The United States Government has certain rights in this invention.

BACKGROUND OF THE INVENTION

The field of the invention is magnetic resonance imaging (MRI) methods and systems. More particularly, the invention relates to quantifying and classifying MRI images of atherosclerotic plaques (coronary artery, carotid artery, aorta, etc.).

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, $M_z$, may be rotated, or "tipped", into the x-y plane to produce a net transverse magnetic moment $M_t$. A signal is emitted by the excited spins after the excitation signal $B_1$ is terminated, this signal may be received and processed to form an image.

When utilizing these signals to produce images, magnetic field gradients ($G_x$ $G_y$, and $G_z$) are employed. Typically, the region to be imaged is scanned by a sequence of measurement cycles in which these gradients vary according to the particular localization method being used. The resulting set of received MR signals are digitized and processed to reconstruct the image using one of many well known reconstruction techniques.

Coronary atherosclerosis is the main contributing factor to ischemic heart disease, the leading cause of mortality in developed countries. Characterization of atherosclerotic plaque structure in coronary arteries is an important factor in assessing susceptibility to acute coronary syndromes. Noninvasive computed tomography (CT) may provide differentiation between calcified and non-calcified plaques in patients at the expense of ionizing radiation exposure. Noninvasive high-resolution MRI has been used in-vivo to monitor changes in burden and composition of human carotid arteries and aortic plaques. Multicontrast MRI as disclosed in U.S. Pat. No. 4,945,478 has been used for classification of atherosclerotic plaque components. Qualitative assessment of plaque composition using pattern recognition was performed on human aortas using $T_1$, $T_2$, and proton density weighted MR images. Normal wall (media), lipid-rich plaques, and fibrous plaques were differentiated with a clustering algorithm.

Multicontrast MRI methods employ different pulse sequences to obtain multiple images of the subject artery. Each pulse sequence is chosen to "weight" the reconstructed magnitude image in such a manner that it highlights, or images, one of the atherosclerotic tissue class types involved in the disease process. To evaluate a disease such as atherosclerosis requires combining together structural information as well as functional information. Structural information includes characteristics of the vessel such as its shape in three dimensions, its location with respect to other structures, and its degree of vessel occlusion, or narrowing. Such structural information may be obtained from any number of different MRI pulse sequences. Functional information involves identification and quantification of the various soft tissue types involved in the disease process. Functional information derived from multicontrast MR images provides information regarding the physiological stage of the disease process.

SUMMARY OF THE INVENTION

The present invention is a multicontrast MRI method in which a plurality of images of a subject are acquired using a corresponding number of different pulse sequences chosen to contrast a corresponding number of tissue types; producing a different color image for each of the plurality of acquired images, combining the plurality of different color images to form a single, color composite MR image, and analyzing the color composite MR image to classify different components of the subject based on color. Cluster analysis may be used to segment the color composite MR image, where each subject component to be segmented is established by a preset range of color values determined by prior measurement of that component.

BRIEF DESCRIPTION OF THE DRAWINGS

FIG. 8 is a table showing the results of different methods for identifying plaque components.

DESCRIPTION OF THE PREFERRED EMBODIMENT

Two embodiments of the invention are described, an ex-vivo embodiment using a very high field MRI system, and an in-vivo embodiment using a clinical MRI system.

The ex-vivo embodiment was performed on a Bruker 9.4T, 89 mm bore MR system with gradient system of 1000 mT/m and rise time of 100 µs (Bruker Instruments, Billerica, Mass.). Twelve human coronary artery specimens 1.28 cm long were imaged using a 10 mm birdcage rf coil.

The specimens were imaged at 37° C. Each specimen was washed and placed in a 8 mm polyethylene tube, filled with Fomblin solution (perfluoropolyether, Ausimont USA Inc, Morristown, N.J.) and sealed to prevent air bubbles. The use of Fomblin limits tissue dehydration and susceptibility effects on the surface of the specimen; it does not have residual MR signal and does not interfere with signal from various biological tissue. MR imaging was performed using 3D fast spin-echo (FSE) sequence with isotropic voxel of 39×39×39 μm³ (field-of-view (FOV) of 1.0 cm). Some of the samples were larger and required FOV of 1.28 cm (voxel size of 50×50×50 μm³). A multicontrast-weighted series of images were acquired. A proton density weighted (PDW) image was acquired with a pulse repetition rate (TR) of 2000 ms and an echo time (TE) of 9 ms. A T1 weighted (T1 W) image was then acquired with TR=500 ms and TE=9 ms, followed by a T2 weighted (T2W) image acquisition at TR=2000 ms and TE=25 ms. The FSE imaging was performed with an echo-train length of 4 and an acquisition matrix size of 256³. Acquisition time was 8 hours for PDW and T2W imaging and 2 hours for T1W imaging. The position and size of the 3D volume was not changed from one M acquisition (T1W, PDW, T2W) to the other so that the three images are registered with each other spatially.

Figure 1:
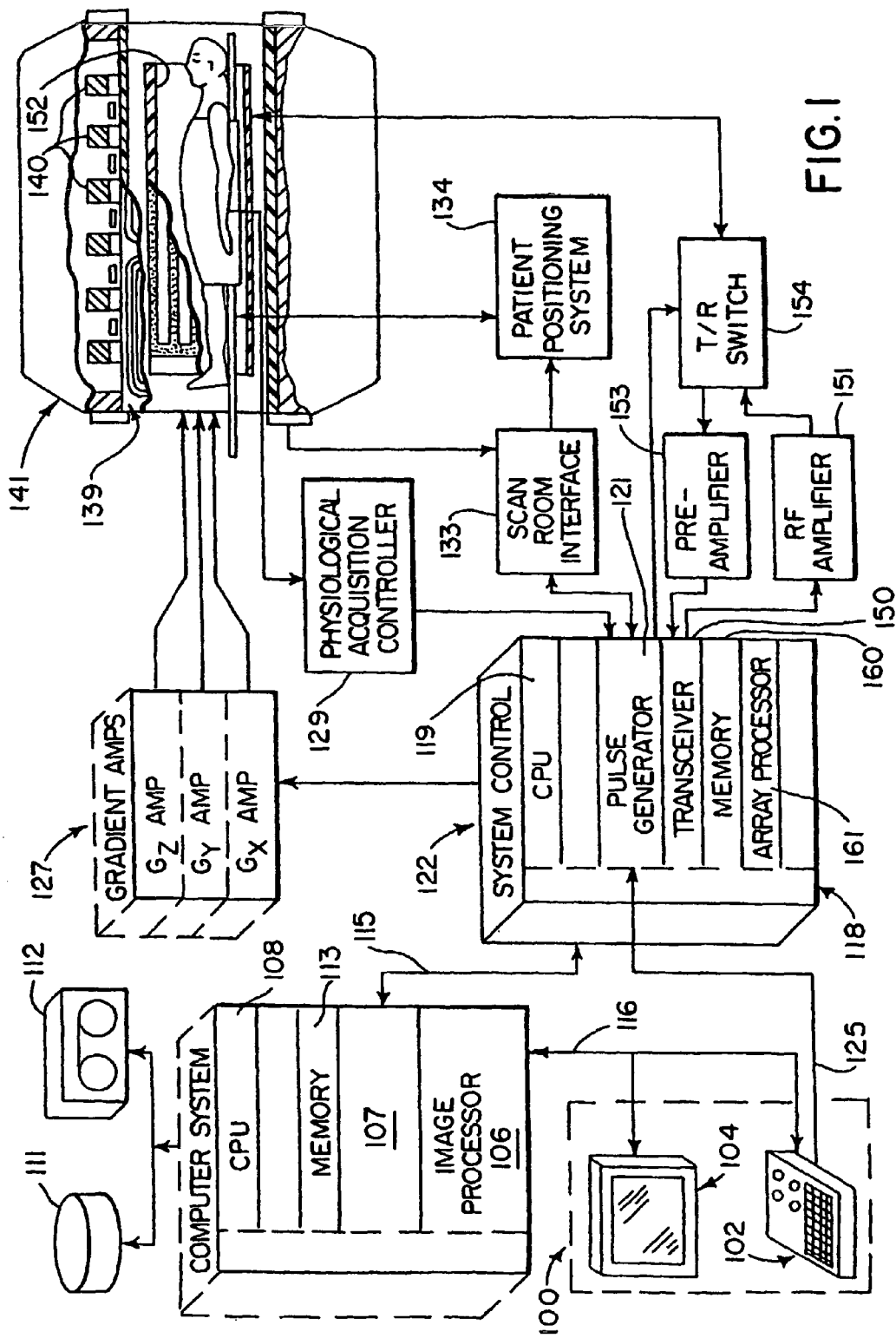
FIG. 1 is a block diagram of an MRI system which employs the present invention.

Referring first to FIG. 1, there is shown the major components of a clinical MRI system which is employed to practice the in-vivo embodiment of the invention. In the preferred embodiment a 1.5T Siemens Sonata whole body MR system (Siemens AG, Erlanger, Germany) is employed with maximum gradient amplitude of 40 mT/m and slew rate of 200 mT/m/ms running Numaris 4.0. The operation of the system is controlled from an operator console 100 which includes a keyboard and control panel 102 and a display 104. The console 100 communicates through a link 116 with a separate computer system 107 that enables an operator to control the production and display of images on the screen 104. The computer system 107 includes a number of modules which communicate with each other through a backplane. These include an image processor module 106, a CPU module 108 and a memory module 113, known in the art as a frame buffer for storing image data arrays. The computer system 107 is linked to a disk storage 111 and a tape drive 112 for storage of image data and programs, and it communicates with a separate system control 122 through a high speed serial link 115.

The system control 122 includes a set of modules connected together by a backplane. These include a CPU module 119 and a pulse generator module 121 which connects to the operator console 100 through a serial link 125. It is through this link 125 that the system control 122 receives commands from the operator which indicate the scan sequence that is to be performed. The pulse generator module 121 operates the system components to carry out the desired scan sequence. It produces data which indicates the timing, strength and shape of the RF pulses which are to be produced, and the timing of and length of the data acquisition window. The pulse generator module 121 connects to a set of gradient amplifiers 127, to indicate the timing and shape of the gradient pulses to be produced during the scan. The pulse generator module 121 also receives patient data from a physiological acquisition controller 129 that receives signals from a number of different sensors connected to the patient, such as ECG signals from electrodes or respiratory signals from a bellows. These signals are used to "gate" the acquisition when imaging moving subjects. And finally, the pulse generator module 121 connects to a scan room interface circuit 133 which receives signals from various sensors associated with the condition of the patient and the magnet system. It is also through the scan room interface circuit 133 that a patient positioning system 134 receives commands to move the patient to the desired position for the scan.

The gradient waveforms produced by the pulse generator module 121 are applied to a gradient amplifier system 127 comprised of $G_x$, $G_y$ and $G_z$ amplifiers. Each gradient amplifier excites a corresponding gradient coil in an assembly generally designated 139 to produce the magnetic field gradients used for position encoding acquired signals. The gradient coil assembly 139 forms part of a magnet assembly 141 which includes a polarizing magnet 140 and a whole-body RF coil 152. A transceiver module 150 in the system control 122 produces pulses which are amplified by an RF amplifier 151 and coupled to the RF coil 152 by a transmit/receive switch 154. The resulting MR signals radiated by the excited nuclei in the patient are received by a circularly polarized, six-channel body array local coil (not shown) and coupled through the transmit/receive switch 154 to separate channels in a preamplifier 153. The amplified MR signals are demodulated, filtered, and digitized in the receiver section of the transceiver 150. The transmit/receive switch 154 is controlled by a signal from the pulse generator module 121 to electrically connect the RF amplifier 151 to the coil 152 during the transmit mode and to connect the preamplifier 153 to the local coil during the receive mode.

The MR signals picked up by the local RF coil are digitized by the transceiver module 150 and transferred to a memory module 160 in the system control 122. When the scan is completed and an entire array of data has been acquired in the memory module 160, an array processor 161 operates to Fourier transform the data into an array of image data. This image data is conveyed through the serial link 115 to the computer system 107 where it is stored in the disk memory 111. In response to commands received from the operator console 100, this image data may be archived on the tape drive 112, or it may be further processed by the image processor 106 and conveyed to the operator console 100 and presented on the display 104.

Figure 6:
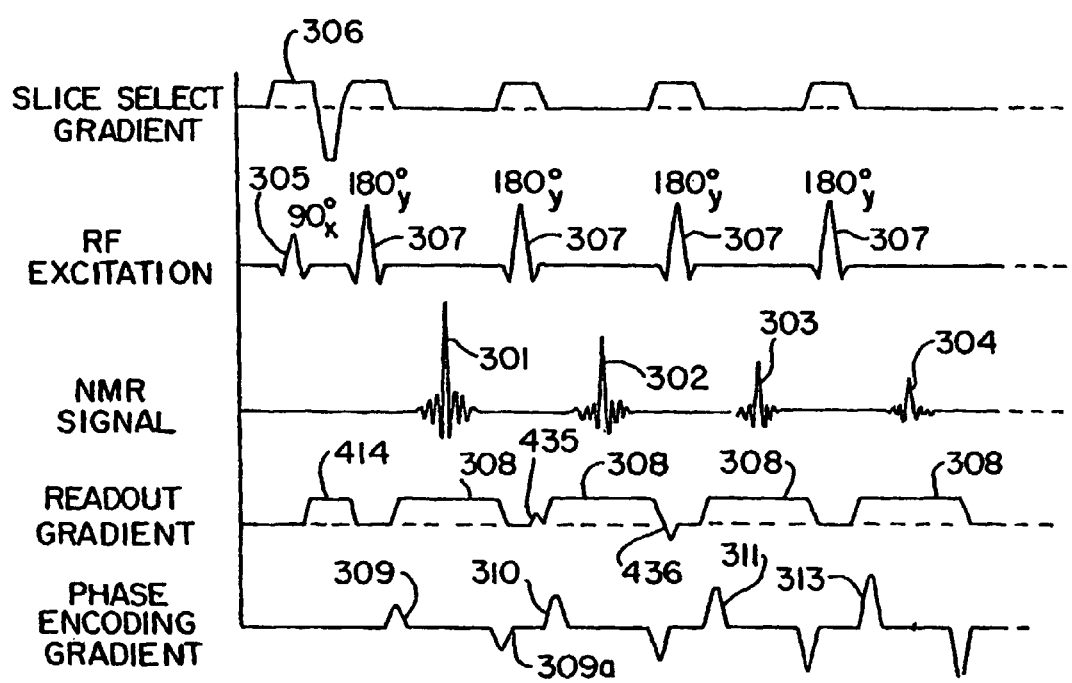
FIG. 6 is a graphic illustration of a preferred pulse sequence performed by the MRI system of FIG. 1.

Referring particularly to FIG. 6, the fast spin echo MR pulse sequence employed to practice the preferred embodiment of the invention is a 2DFT RARE sequence in which four MR echo signals 301-304 are acquired. These MR echo signals are produced by a 90° RF excitation pulse 305 which is generated in the presence of a $G_z$ slice select gradient pulse 306 to provide transverse magnetization in a slice through the subject. This transverse magnetization is refocused by each of four selective 180° RF echo pulses 307 to produce the MR spin echo signals 301-304 phase encoded by respective $G_y$ phase encoding pulses 309-313. The magnitude of each phase encoding pulse is different, and it is stepped through 256 values to acquire 256 separate views during a complete scan. Each MR spin echo signal is acquired by digitizing 256 samples of each signals and as a result, at the completion of a scan for one image, a 256 by 256 pixel image is produced by performing a 2D Fourier transformation on the acquired data.

As with the above described ex-vivo embodiment, three images are acquired of the subject arteries using pulse sequences which weight the acquired MR signals differently. The scan parameters are selected to provide a proton density weighted (PDW) image, a $T_1$ weighted (T1W) image, and a $T_2$ weighted (T2W) image. A double inversion recovery preparatory pulse sequence is employed prior to each FSE pulse sequence to suppress the signals from blood and cardiac gating is employed throughout the acquisitions to minimize vessel motion artifacts.

It should be apparent to those skilled in the art that other pulse sequences may be used to acquire the multicontrast weighted images. For example, time-of-flight (TOF) MR, gradient-recalled echo $T_2$ MR, $T_1$ contrast MR magnetization transfer weighting, diffusion weighted MR, steady state free precision weighted MR and others may be used to enhance signals from particular tissue types of interest. As will be discussed below, by acquiring three differently weighted images of the subject, up to eight different tissue types are differentiated using the present invention. Additional images with different weighting characteristics may also be employed to increase the number and types of tissues that are differentiated, or fewer contrast images may be acquired to shorten the scan time when fewer tissue types need to be differentiated.

Figure 2A:
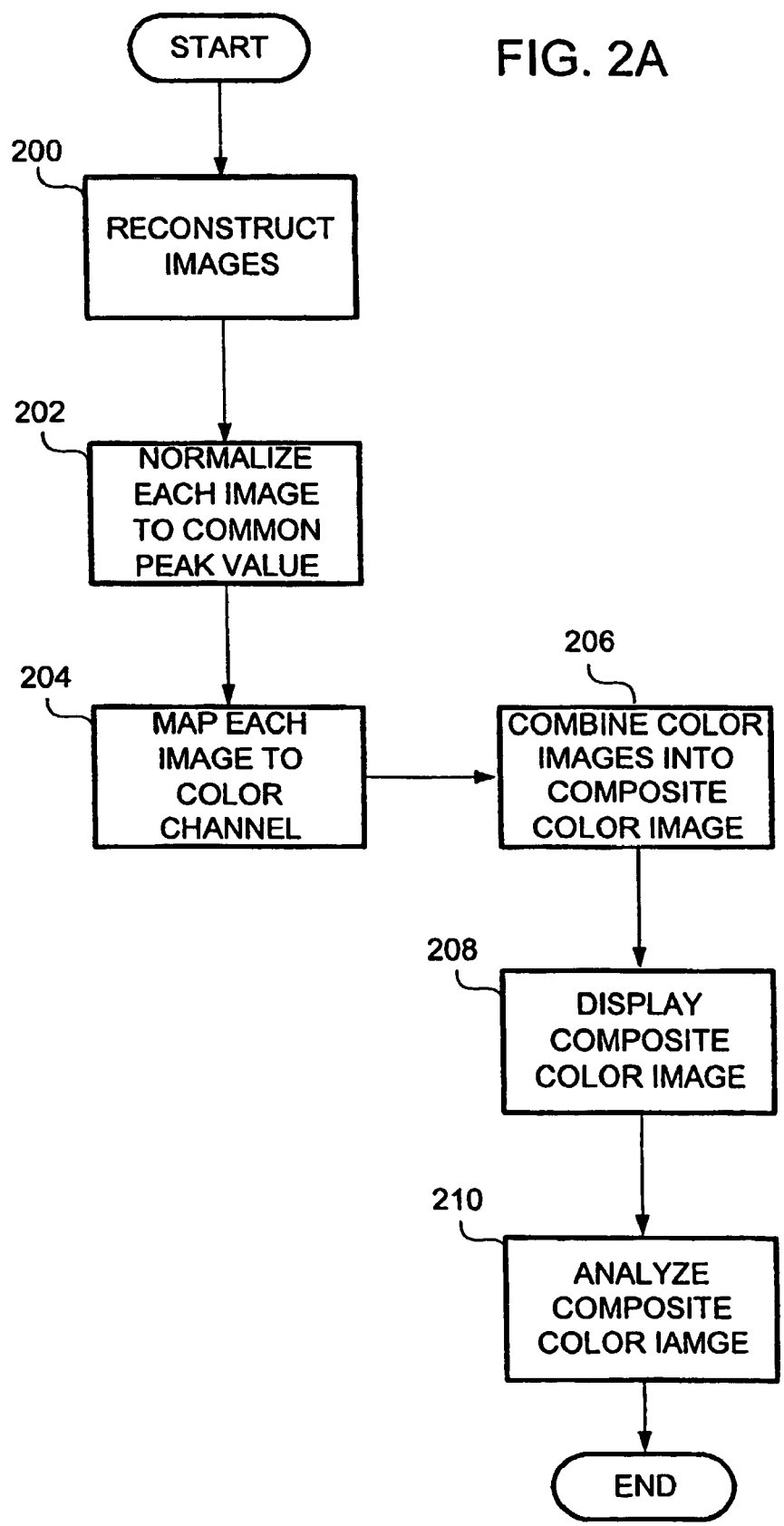
FIG. 2 is a flow chart of the steps in the preferred method of practicing the present invention.

The processing of the acquired ex-vivo and in-vivo images is the same. Referring particularly to FIG. 2A, after the images are acquired as described above they are reconstructed in the normal fashion (3DFT or 2DFT) to produce a set of three magnitude images as indicated at process block 200. These images may be displayed separately and the magnitude of each value therein controls the brightness of a corresponding pixel in a gray scale image of the subject. These gray scale images will differ from each other due to the different weighting factors used during their acquisition.

The next step as indicated at process block 202 is to normalize each gray scale image such that each contributes equally to the composite color image to be formed in following steps. This is accomplished by setting the values of the brightest pixels in each gray scale image to the same value and adjusting the values of the other pixels in their respective images a corresponding amount. This normalization step gives equal weight to the three images by giving their intensity values the same scale.

Figure 4:
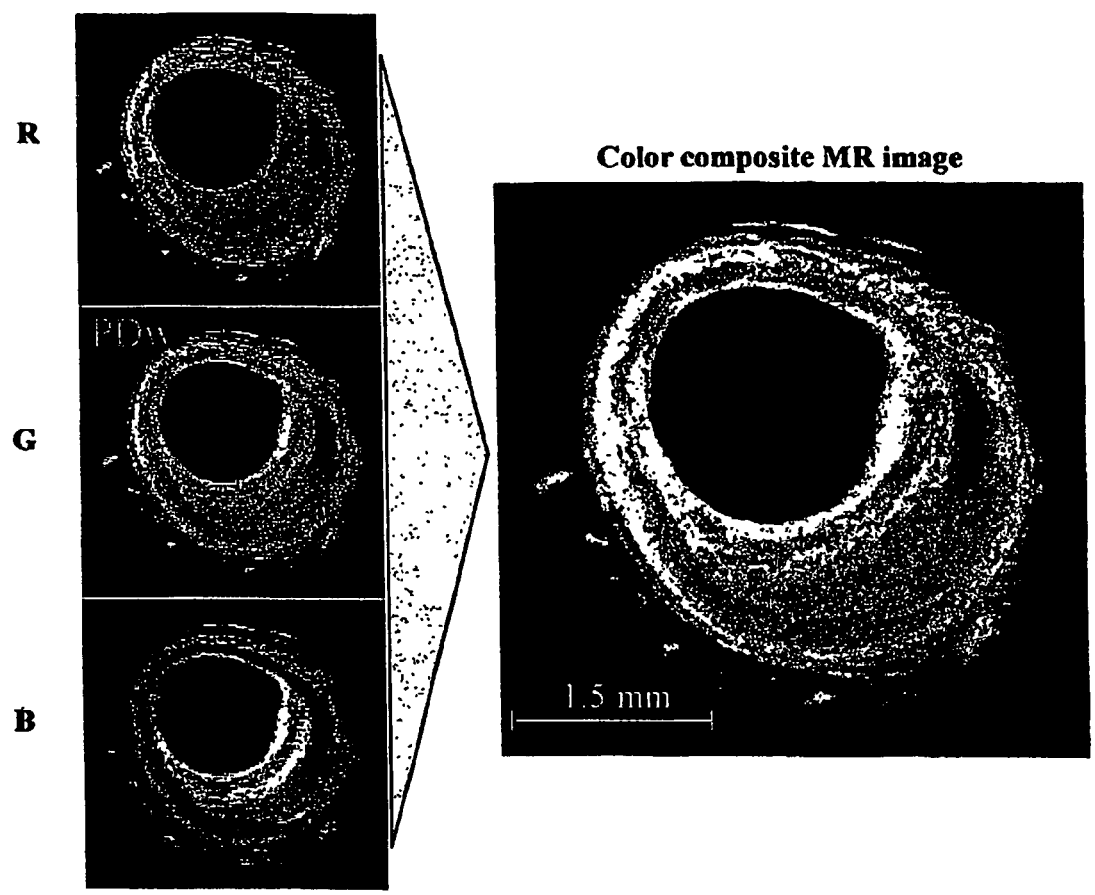
FIG. 4 is an exemplary color composite image produced by the method of FIG. 2.

As indicated at process block 204, the three, normalized gray scale images are then each mapped to a separate color channel. In the preferred embodiment, the PDW image is mapped to the green channel, the T2W image is mapped to the red channel, and the T2W image is mapped to the blue channel. These three color images are then combined as indicated at process block 206 to form a single composite color image that may be displayed as indicated at process block 208 and as shown in FIG. 4. The three colors optically combine at each image pixel to produce a displayable color indicative of the relative amounts of each color at that image pixel. In the ex-vivo embodiment the three color images are registered and their combination is merely the mapping of corresponding pixel values in the three color images to the corresponding pixel in the composite color image. Because the subject may move during the in-vivo acquisition, the three color images may require a separate registration step prior to their combination. Numerous registration methods which align features in anatomic images are known in the art and may be used if needed.

While the display of the composite color image provides significant clinical information, this image can also be analyzed automatically as indicated at process block 210 to provide quantitative information regarding the imaged tissue types. The objective method is preferred in order to segment and quantify plaque components.

Figure 7:
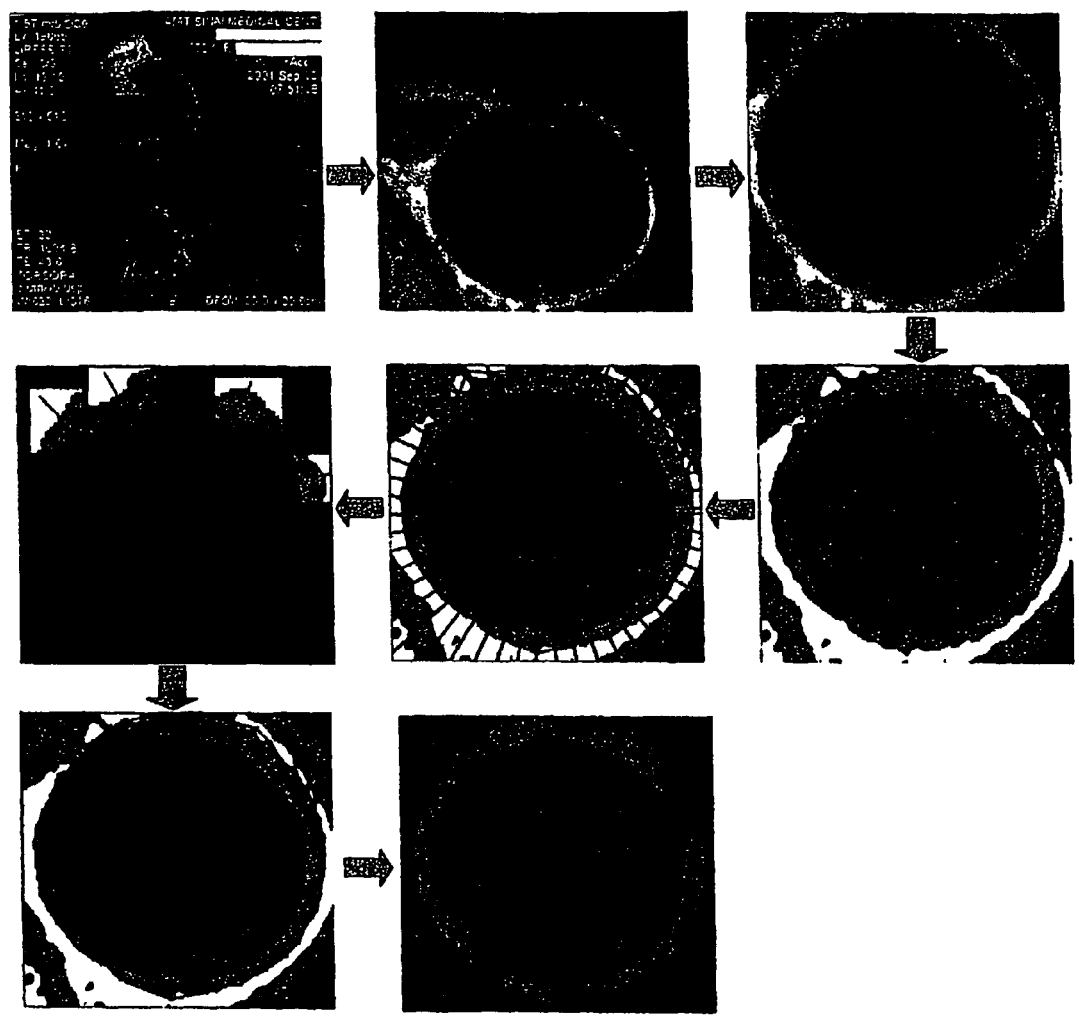
FIG. 7 is a sequence of images A-H showing the steps employed to analyze a color composite image.

Referring particularly to FIGS. 2B and 7, the analysis process begins by selecting a region of interest to be analyzed as indicated at process block 212. This is done by the user who selects a square region centered on the vessel of interest from the first slice in the study as shown in FIG. 7A. As indicated by process block 214, the outline of the vessel lumen is then detected and the image is cropped around this detected lumen as shown in FIGS. 7B and 7C. This is performed on each slice in the study. An active contour (or "snake") method such as that described by Kass, M. et al: "Snakes: Active Contour Models", Int. Journal of Computer Vision 1 (1987) 321-331 is used. A snake consists of a set of points that define an elastic curve over which energy is defined. The system's overall energy is derived from the energy encapsulated in the snake model itself and the energy supplied from the image under consideration. Minimizing the system's energy function causes the active contour to converge to a stable state and reveal salient image characteristics as illustrated in FIG. 7A.

As indicated at process block 216, the region surrounding the vessel lumen is then segmented to identify the different tissue types present as shown in FIG. 7D. A cluster analysis method is used to segment the image into lumen, plaque and outer wall tissue components. Cluster analysis is an exploratory data-partitioning technique for solving classification problems of this type. Its aim is to sort data into groups, or clusters, so that the degree of association is strong between members of the same cluster and weak between members of different clusters. Each cluster thus describes, in terms of the data collected, the class to which its members belong. In the application of cluster analysis to the composite color image, data clusters serve to delineate the different tissue components according to their color. The K-means method of partitional cluster analysis described by Forgy, E. "Cluster analysis of multivariate data: Efficiency versus interpretability of classification", *Biometric,* 1965; 21:768-780, is used in the preferred embodiment.

Our implementation of cluster analysis exploits two aspects of the image pixel data, the image's color variance (cluster compactness in color space) and spatial information (local pixel discontiguity) as described by Theiler J. Gisler G. "A Contiguity-Enhanced k-Means Clustering Algorithm For Unsupervised Multispectral Image Segmentation," *Proc SPIE* 1997; 3159:108-118.

Figure 3:
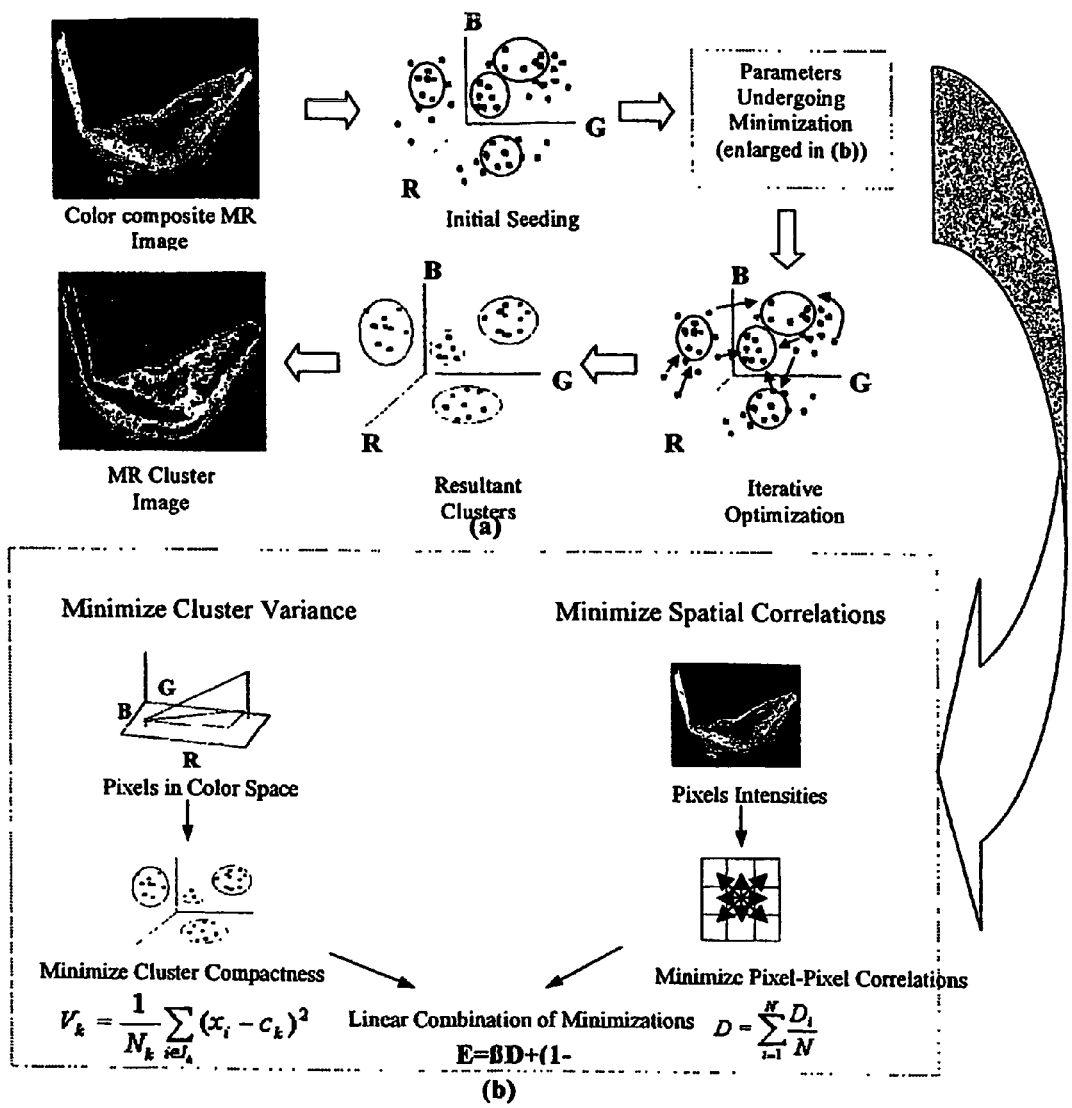
FIG. 3 is a pictorial representation of the cluster analysis step which forms part of the method of FIG. 2.

This method is illustrated in FIG. 3. The number of clusters, their seed points and associated tissue type for the cluster analysis algorithm were determined automatically for each MR image through the use of established ranges of color values for each of the tissue types. These ranges were obtained from the color composite MR images of a representative specimen. Presence of specific tissue components was determined automatically by matching pixel values within the image of interest to the representative color ranges, thus establishing number of clusters and values for their seed points. The defining color ranges for tissue types were only approximations and served to automatically initialize the number of clusters and seed points in the K-means cluster analysis of all specimens without reference to other image data or histopathology slices. The acceptable data metric (measure of degree of association between collections of pixels in color space) was the shortest distance in space (Euclidian). This data metric was applied to all MR images.

Referring again to FIGS. 2B and 7, the next step in the analysis process as indicated by process block 218 is to detect the outer border of the plaque. This is achieved as illustrated in FIG. 7E by radiating line-profiles of the clustered image outward from the center of the lumen. Each such line-profile indicates the radial distance between the lumen border and the outer border of the plaque. From this information, area(s) where the plaque thickness deviates dramatically from the average plaque thickness is detected as indicated at process block 220 and illustrated in FIG. 7F. As indicated at process block 222, further cluster analysis is iteratively applied on such detected area(s) at varying scales to produce a well-defined plaque region as illustrated in FIG. 7G. This well-defined plaque region may then be extracted from the image as shown in FIG. 7H. When stacked with other cluster-analyzed color composite images in the study, a 3D image of the plaque is produced in which different colors indicate different plaque constituents.

Figure 5:
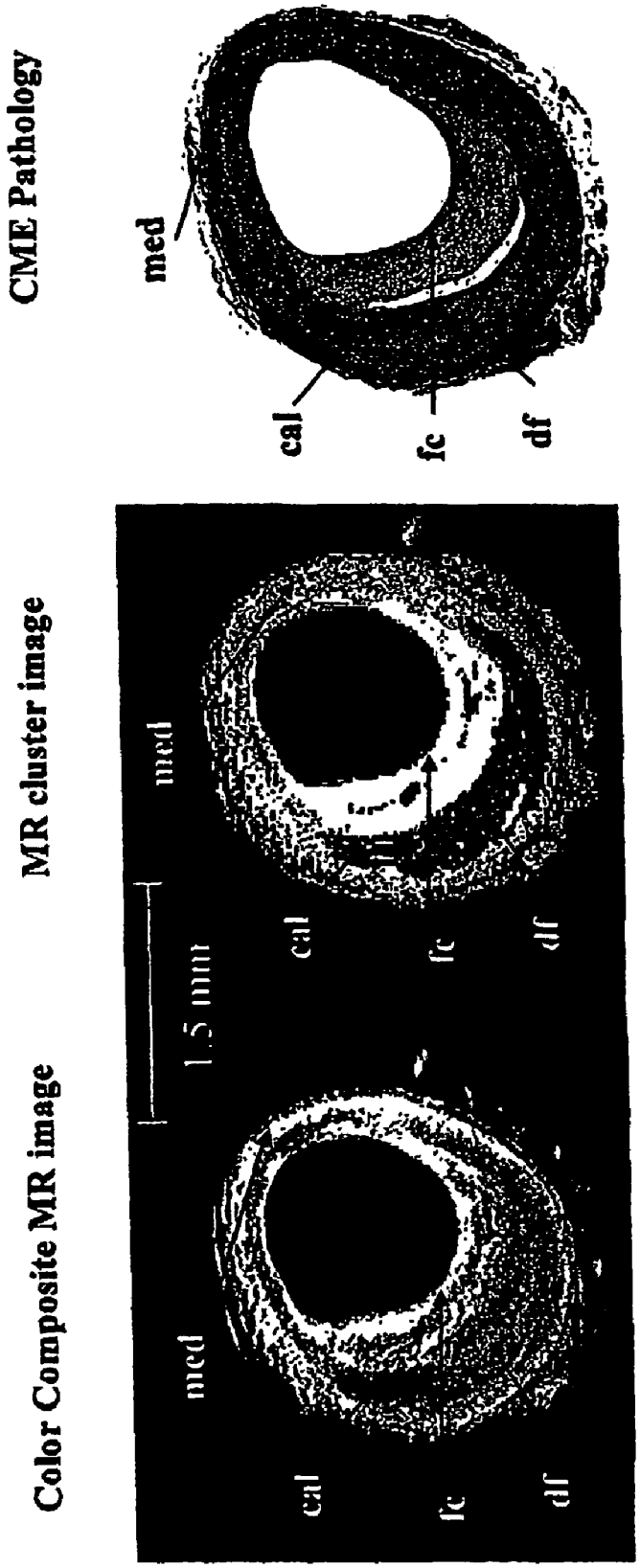
FIG. 5 is an exemplary color composite image, a cluster image and a real image of a section of an artery after histological preparation and staining.

Since different atherosclerotic plaque components possess distinct signal strength in each of the T1W, T2W and PDW MR images, the unanalyzed composite image has a distinct color distribution particular to the type of tissue present in the specimen as shown in FIG. 4. This image provides a qualitative means to assess plaque composition on specimens that span the entire range of AHA plaque types I-VI. Table 1 shows the classification results. The agreement between manually traced histopathology and color composite or cluster-analyzed MR images was good or very good; the agreement between histopathology and conventional gray scale MR images (T2W) was moderate. The color composite method was capable of enhancing subtle variations in gray-scale luminance thereby making more evident various tissue components. An example of AHA type Vb-Vc plaque with the corresponding color composite MR image, cluster-analyzed color composite MR image, and histopathology is shown in FIG. 5.

TABLE 1

Qualitative Analysis of Coronary Plaques (AHA Classification)

| Comparison Type | Parameter Name | | |
|---|---|---|---|
| | Cohen's Kappa | Percent Of Agreement | P-Value |
| Histopathology Tracing & Cluster-Analyzed MRI | 0.89 | 92 | <0.0001 |
| Histopathology Tracing & Color Composite MRI | 0.78 | 83 | 0.0001 |
| Histopathology Tracing & T2W Grayscale MRI | 0.42 | 67 | 0.0268 |

Type I-III - isolated macrophage foam cells, intercellular lipid accumulation.
Type IV-Va - lipid/necrotic core and fibrotic layer.
Type Va-Vc - calcific or fibrotic.
Type VI - complex with surface defect, hematoma-hemorrhage, thrombus.

Quantitative comparison data (correlation and Bland-Altman analysis) for each individual plaque component is shown in FIG. 8. Individual plaque components' areas are computed as a percentage of total wall area. There is a high degree of correlation between histopathology tracings and cluster-analyzed high-resolution MR images for the six identified tissue components (loose fibrous, media, dense fibrous, fibro-cellular (cap), thrombus, lipid/necrotic core). In this table:
  r=correlation value;
  bias=mean value of differences between paired measurements; and
  lim=limits of agreement between paired measurements (95% confidence interval).

It should be apparent that variations are possible from the preferred embodiment described above without departing from the spirit of the invention. For example, other imaging modalities may be used alone or in combination to acquire a plurality of images that are weighted for different plaque tissue types. Also, these separate weighted images are mapped to separate color channels in the preferred embodiment, but if analysis is to be performed, the magnitudes in these images can be viewed as separate components of a composite vector image which is formed by their combination. Analysis is performed on the composite vector image and the resulting identified tissue types may be displayed in different colors.

The invention claimed is:

1. A method for producing an image with a magnetic resonance imaging (MRI) system, the steps comprising:
   acquiring a plurality of image data sets from a subject using the MRI system, each image data set being acquired with a different pulse sequence prescription that weights the acquired image data sets differently;
   reconstructing a plurality of images of the subject from the acquired image data sets;
   mapping each of the plurality of images to a different color; and
   combining each mapped color image to form a single composite color image.

2. The method as recited in claim 1 which includes displaying the composite color image.

3. The method as recited in claim 1 which includes analyzing the composite color image to identify a plurality of different tissue types therein.

4. The method as recited in claim 3 in which the analysis is a cluster analysis of pixels in the composite color image based on the color of the pixels.

5. The method as recited in claim 3 in which the subject is an artery and the tissue types are found in atherosclerotic plaque.

6. The method as recited in claim 1 in which the different pulse sequence prescriptions include a $T_1$ weighted prescription, a $T_2$ weighted prescription and a proton density weighted prescription.

7. The method as recited in claim 6 in which the composite color image is analyzed based on the color of pixels in the composite color image to identify a plurality of different tissue types therein.

8. The method as recited in claim 1 which includes
   normalizing each of the plurality of images to equally weight the magnitudes of the plurality of images prior to forming the composite color image.

9. A method for analyzing atherosclerotic plaque in the blood vessel of a subject, the steps comprising:
   a) acquiring a plurality of image data sets using a magnetic resonance imaging (MRI) system, each image data set being acquired with a pulse sequence have a prescription that weights the acquired image data sets for different atherosclerotic tissue class types;
   b) reconstructing a plurality of images of the subject using the acquired image data sets;
   c) mapping each of the plurality of images to a different color;
   d) combining each mapped color image to form a single composite color image; and
   e) analyzing the composite color image to identify a plurality of different atherosclerotic tissue types therein.

10. The method as recited in claim 9 in which the different pulse sequence prescriptions include a $T_1$ weighted prescription, a $T_2$ weighted prescription and a proton density weighted prescription.

11. The method as recited in claim 9 which includes calculating a magnitude image from each of the plurality of images and normalizing each magnitude image to equally weight the magnitudes therein prior to forming the composite color image therewith.

12. The method as recited in claim 9 in which step d) includes registering the mapped color images before they are combined.

13. The method as recited in claim 9 in which step e) includes performing a cluster analysis of the colors in said composite color image.

14. The method as recited in claim 9 in which step e) includes performing an active contour analysis of the colors in said composite color image.

15. The method as recited in claim 9 in which step e) includes i) performing an active contour analysis of the composite color image to identify the lumen of the blood vessel depicted therein; and ii) performing cluster analysis on the region surrounding the identified lumen to identify a plurality of different tissue types therein.

16. The method as recited in claim 15 in which step e) further includes:

iii) locating the outer border of plaque tissues;

iv) locating regions in which the plaque thickness deviates substantially from the average plaque thickness around the lumen; and v) performing further cluster analysis on said located regions.

17. A method for analyzing atherosclerotic plaque in the blood vessel of a subject, the steps comprising:

a) acquiring a plurality of images of the blood vessel, each image being acquired with a prescription that weights the acquired data for different atherosclerotic tissue types;

b) mapping each acquired image to a different vector component image;

c) combining each mapped vector component image to form a single composite vector image in which each pixel is the vector sum of the corresponding vector component values in the mapped vector component images; and d) analyzing the composite vector image to identify a plurality of different atherosclerotic tissue types therein.

18. The method as recited in claim 17 in which step a) is performed on a magnetic resonance imaging system with pulse sequences that are prescribed to weight the acquired data for different atherosclerotic tissue types.

19. The method as recited in claim 18 in which the prescriptions include a $T_1$ weighted prescription, a $T_2$ weighted prescription, and a proton density weighted prescription.

* * * * *

UNITED STATES PATENT AND TRADEMARK OFFICE
CERTIFICATE OF CORRECTION

PATENT NO. : 7,764,814 B2 Page 1 of 1
APPLICATION NO. : 10/562745
DATED : July 27, 2010
INVENTOR(S) : Fayad et al.

It is certified that error appears in the above-identified patent and that said Letters Patent is hereby corrected as shown below:

Column 8, line 39, Claim 9, "subiect" should be --subject--.

Signed and Sealed this

Thirty-first Day of August, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,764,814 B2 | Page 1 of 1 |
| APPLICATION NO. | : 10/562745 | |
| DATED | : July 27, 2010 | |
| INVENTOR(S) | : Fayad et al. | |

It is certified that error appears in the above-identified patent and that said Letters Patent is hereby corrected as shown below:

Column 3, line 18, "M" should be --MR--.

Signed and Sealed this

Twenty-eighth Day of September, 2010

David J. Kappos
*Director of the United States Patent and Trademark Office*